United States Patent
Katti et al.

(10) Patent No.: US 6,635,235 B1
(45) Date of Patent: Oct. 21, 2003

(54) BIFUNCTIONAL CHELATING AGENT FOR THE DESIGN AND DEVELOPMENT OF SITE SPECIFIC RADIOPHARMACEUTICALS AND BIOMOLECULE CONJUGATION STRATEGY

(75) Inventors: Kattesh V. Katti, Colubmia, MO (US); Kandikere R. Prabhu, Bangalore (IN); Hariprasad Gali, Columbia, MO (US); Nagavara Kishore Pillarsetty, Columbia, MO (US); Wynn A. Volkert, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/602,487

(22) Filed: Jun. 23, 2000

Related U.S. Application Data

(60) Provisional application No. 60/141,047, filed on Jun. 24, 1999.

(51) Int. Cl.$^7$ .................. A61K 51/00; A61M 36/14
(52) U.S. Cl. ............ 424/1.69; 424/1.11; 424/1.65; 424/9.1; 534/10; 534/11; 534/14; 534/15
(58) Field of Search ................ 534/7, 10–16; 424/1.11, 1.65, 9.1, 1.69; 568/8

(56) References Cited

PUBLICATIONS

Scott R. Gilbertson et al. Synthesis of Phosphine–Rhodium Complexes Attached to a Standard Peptide Synthesis Resin (1996), Organometallics, vol. 15, pp. 4678–4680.

Shuang Liu et al. $^{99m}$Tc Labeling of Highly Potent Small Peptides (1997), Bioconjugate Chem. vol. 8, pp. 621–636.

J. Lister–James, et al. Small peptides radiolabed with $^{99m}$Tc (1996), QJ Nucl. Med. vol. 40, pp. 221–233.

Scott R. Gilbertson et al. Versatile Building Block for the Synthesis of Phosphine–Containing Peptides: The Sulfide of Diphenylphosphinoserine (1994), J Am, Chem. Soc., vol. 116, pp. 4481–4482.

C. Jeffrey Smith, et al. Synthesis and Coordination Chemistry of the First Water–Soluble Dithio–Bis(phosphine) Ligands . . . (1997), Inorg. Chem. vol. 36, pp. 3928–3935.

C. Jeffrey Smith, et al. Syntheses and Characterization of Chemically Flexible, Water–Soluble Dithio–Bis(phosphine) Compounds . . . (1997), Inorg. Chem, vol. 36, pp. 1786–1791.

C.J. Smith, et al. In Vitro and In Vivo Characterization of Novel Water–Soluble Dithio–Bisphosphine $^{99m}$Tc Complexes (1997), Nuclear Medicine & Biology, vol. 24, pp. 685–691.

Primary Examiner—Dameron L. Jones
(74) Attorney, Agent, or Firm—Kohn & Associates, PLLC

(57) ABSTRACT

There is provided a method of labeling a biomolecule with a transition metal or radiometal in a site specific manner to produce a diagnostic or therapeutic pharmaceutical compound by synthesizing a $P_2N_2$-bifunctional chelating agent intermediate, complexing the intermediate with a radio metal or a transition metal, and covalently linking the resulting metal-complexed bifunctional chelating agent with a biomolecule in a site specific manner. Also provided is a method of synthesizing the —$PR_2$ containing biomolecules by synthesizing a $P_2N_2$-bifunctional chelating agent intermediate, complexing the intermediate with a radiometal or a transition metal, and covalently linking the resulting radio metal-complexed bifunctional chelating agent with a biomolecule in a site specific manner. There is provided a therapeutic or diagnostic agent comprising a —$PR_2$ containing biomolecule.

5 Claims, 5 Drawing Sheets

BIFUNCTIONAL CHELATING AGENT FOR THE DESIGN AND DEVELOPMENT OF SITE SPECIFIC RADIOPHARMACEUTICALS AND BIOMOLECULE CONJUGATION STRATEGY

CROSS REFERENCE TO RELATED APPLICATIONS

This application claims the benefit of priority of U.S. Provisional Patent Application Serial No. 60/141,047, filed Jun. 24, 1999, and which is incorporated herein by reference.

GRANT INFORMATION

Research in this application was supported in part by a grant from the Department of Energy (DEFG02-89ER60875). The government has certain rights in the invention. Research in this application was also supported in part by a grant from DuPont Pharmaceuticals (C-5-35122; and C-5-31488).

TECHNICAL FIELD

The present invention relates to metallated biomolecules. More specifically, the present invention relates to the development of a new strategy for synthesizing biomolecules that can be used to form structure-specific metallated biomolecules.

BACKGROUND OF THE INVENTION

The transition metal chemistry of phosphines is diverse, resulting in a myriad of coordination compounds. The wealth of available data on the coordination chemistry of rhenium has provided a strong impetus in extending the chemistry to its diagonally related congener technetium-99. In fact, the demonstration that phosphine ligands produce well-defined, in vitro/in vivo stable complexes with technetium-99m (a γ-emitter with 141 keV and $t_{1/2}$=6.2 h) has resulted in the development of two Tc-99m-based radiopharmaceuticals being currently used for myocardial imaging in humans. [DeRosch et al., 1992; Forster et al., 1992]. Because most human cancer cells express a certain affinity for biomolecular vectors such as peptides or proteins, it is conceivable that radiolabeled receptor-avid peptides will provide new vehicles for delivering diagnostic or therapeutic radiations in site-directed treatments. Radiolabeling of receptor-avid peptides (or other bimolecular vectors) is best carried out by using bifunctional chelating agents. Radiolabeling with specific radioisotopes is done at the ligating unit of the bifunctional chelating agent, while functionalities such as —COOH or —NCS will incorporate a biomolecular vector within the bifunctional chelating agent to ultimately produce radiolabeled biomolecules. In this context, the utility of phosphines to construct new bifunctional chelating agents is attractive because of the potential applications of these ligands to produce well-defined complexes with radio-isotopes of diagnostic (Tc-99m) and therapeutic (Re-188, Au-199, Rh-105) value.

However, it is recognized that chemical transformations of traditional phosphine ligands (e.g. $Ph_2PCH_2CH_2PPh_2$, dppe or $Me_2PCH_2CH_2Pme_2$, dmpe) into bifunctional chelating agents are a challenge. Aryl phosphines (e.g. dppe) which are oxidatively stable are unsuitable for use under in vivo conditions because of their high lipophilicity. On the other hand, alkyl phosphines are oxidatively so unstable that backbone modification and their use in aqueous media would produce corresponding phosphine oxides. Therefore, in order to utilize the superior ligating properties of phosphine ligands in the construction of new bifunctional chelating agents, new strategies on the overall design of phosphine frameworks were needed.

The rich chemistry of phosphines with transition metals makes them well suited for constructing chelating frameworks on simple and complex molecular structures that can be used to form well-defined metallated biomolecules. Metallated biomolecules, where the metal is bound (chelated) in a site-specific and structure-specific manner, hold important potential for a variety of chemical and biomedical applications, including chiral catalysis and radiopharmaceuticals [Gilbertson et al., 1996; Liu et al., 1997; Lister-James, et al., 1996]. In this context, the utility of phosphines to construct metal chelating frameworks either appended to or incorporated within biomolecular structures at specific positions is particularly attractive.

However, it must be recognized that the incorporation of phosphine functionalities in biomolecules by current synthetic strategies is challenging and usually involves lengthy procedures and harsh reaction conditions that often damage (e.g., reduction with Raney nickel) the biomolecule [Gilbertson et al., 1994]. For example, Gilbertson, et al. 1994, employed a reaction pathway to append diphenylphosphine groups that used a diphenylphosphorous (V) sulfide intermediate. After the P=S derivatized peptide was made, reduction of the P=S to the phosphorous (III) phosphine was accomplished with Raney Ni [3] producing a mixture of products where the desired diphosphine-peptide product was produced in low yields. The resulting diphenylphosphine-peptide conjugate was subsequently used to selectively form the corresponding Rh(III) conjugate [Gilbertson et al., 1994].

Recent efforts have been successful in synthesis of bidentate and multidentate chelation frameworks that contain di-hydroxymethylene-phosphine (HMP) functionalities [i.e., —$P(CH_2OH)_2$] to facilitate formation of new transition metal complexes [Smith and Reddy et al., 1997; Smith and Katti et al., 1997; Smith and Li et al., 1997]. As a result of this work, the first bifunctional chelating agent containing HMP groups was synthesized, characterized, and used as a vehicle to conjugate metals to biomolecules. The synthesis of this bifunctional chelating agent system (i.e., carboxylate derivative of the di-HMP-diamido ($P_2N_2$) tetradentate ligand framework shown in Formula 1) was difficult and proceeded via a —P(V)=O intermediate (similar to the Gillickson —P(V)=S intermediate) that had to be reduced with $LiAlH_4$ to a —$P(III)H_2$ intermediate in route to formation of the —$P(CH_2OH)_2$ groups. However, the reduction conditions used would irreversibly alter most biomolecules precluding this approach for synthesis of most phosphine bioconjugates.

It would therefore be useful to develop HMP-containing ligand frameworks and —$PR_2$ containing biomolecules for use in formulating new diagnostic and therapeutic pharmaceuticals.

BRIEF DESCRIPTION OF THE DRAWINGS

Other advantages of the present invention will be readily appreciated as the same becomes better understood by reference to the following detailed description when considered in connection with the accompanying drawings wherein.

SUMMARY OF THE INVENTION

According to the present invention, there is provided a method of labeling a biomolecule with a transition metal or radiometal in a site specific manner to produce a diagnostic or therapeutic pharmaceutical compound by synthesizing a $P_2N_2$-bifunctional chelating agent intermediate, complexing the intermediate with a radiometal or a transition metal, and covalently linking the resulting metal-complexed and bifunctional chelating agent with a biomolecule in a site specific manner. Also provided is a method of synthesizing the —$PR_2$ containing biomolecules by synthesizing a $P_2N_2$-bifunctional chelating agent intermediate, complexing the intermediate with a radiometal or a transition metal, and covalently linking the resulting radiometal-complexed bifunctional chelating agent with a biomolecule in a site specific manner. There is provided a therapeutic or diagnostic agent comprising a —$PR_2$ containing biomolecule.

DETAILED DESCRIPTION

Generally, the present invention provides a diagnostic or therapeutic compound which has a —$PR_2$ containing biomolecule. The method for making this diagnostic or therapeutic compound is also disclosed by the present invention.

Figure 6:
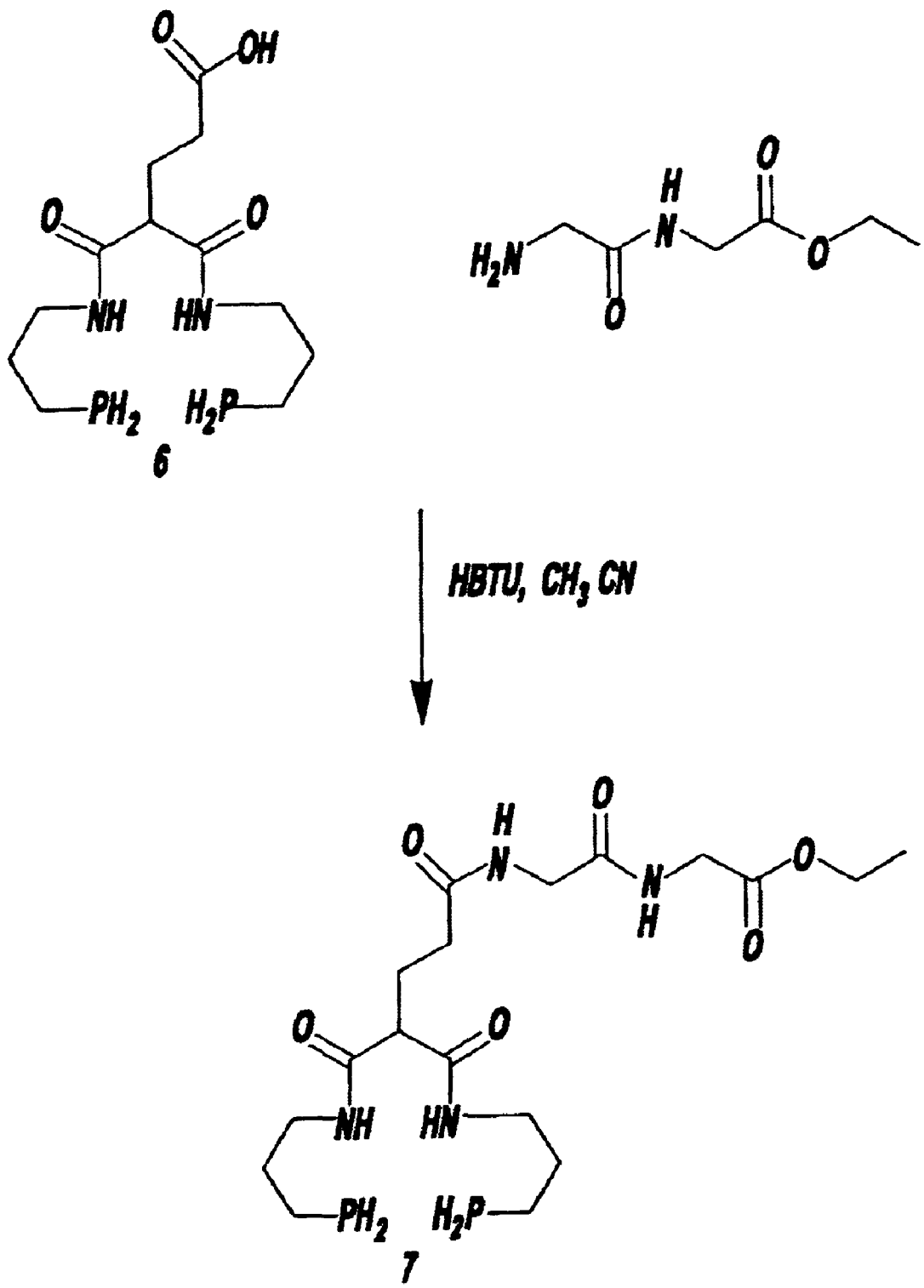
FIG. 6 is a detailed depiction of Scheme 4.
Figure 7:
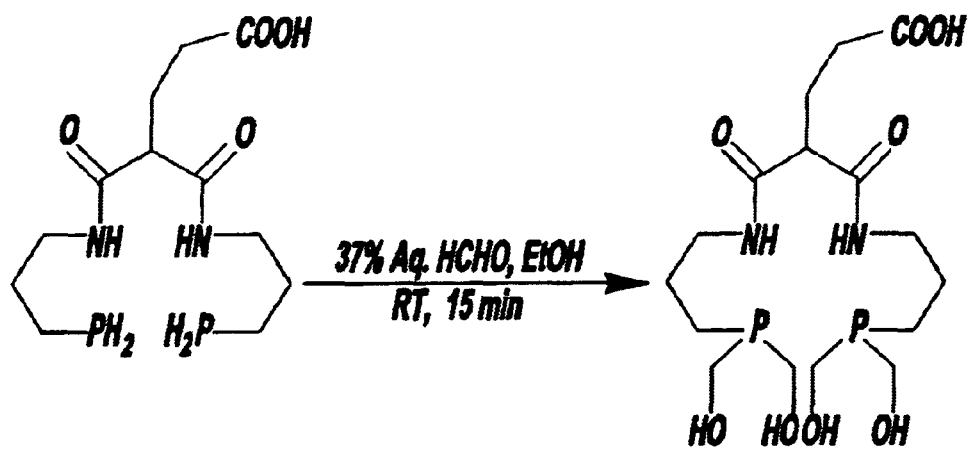
FIG. 7 is a detailed depiction of Scheme 5.

Alkyl substituted phosphines are, in general, oxidatively unstable and, therefore, their backbone chemical modification is difficult especially in the context of appending them on biomolecules (e.g. peptides, proteins and other receptor-avid biomolecules). The present invention utilizes the novel discovery that phosphines, in the form of functionalized phosphorus(III) hydrides, are oxidatively-stable and can be used to achieve chemical modifications. In fact, chemical backbones such as thioethers, amides and amines can be incorporated across —$PH_2$ units without fear of oxidation of the $P^{III}$ center. Further, the carboxylate functionalized ($PH_2$)$_2N_2$—COOH bifunctional chelating agent is stable to reaction conditions that are employed during solid phase peptide synthesis (including treatment with HBTU, piperidine, solutions in DMF and washing the resin with trifluoroacetic acid of specific concentrations) for its incorporation on specific biomolecules including peptides (see Schemes 4 and 5; FIGS. 6 and 7). This order of chemical flexibility and oxidative stability of functionalized $P^{III}$ hydrides present realistic prospects in the design and development of radio-labeled biomolecules for use in site-directed diagnosis and therapy of human cancers.

Figure 1:
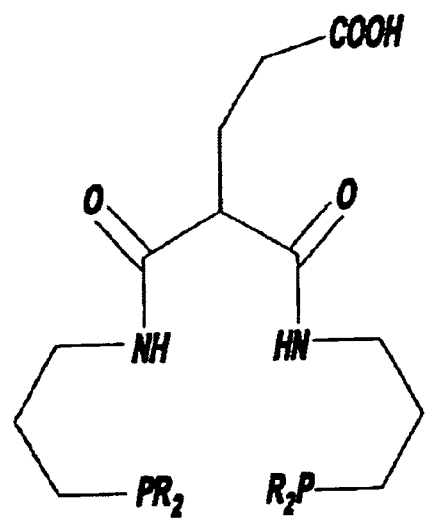
FIG. 1 is the chemical formulation of the $P_2N_2$—COOH bifunctional chelating agent ($P_2N_2$—BFCA) containing two HMP groups (R=CHOH)
Figure 3:
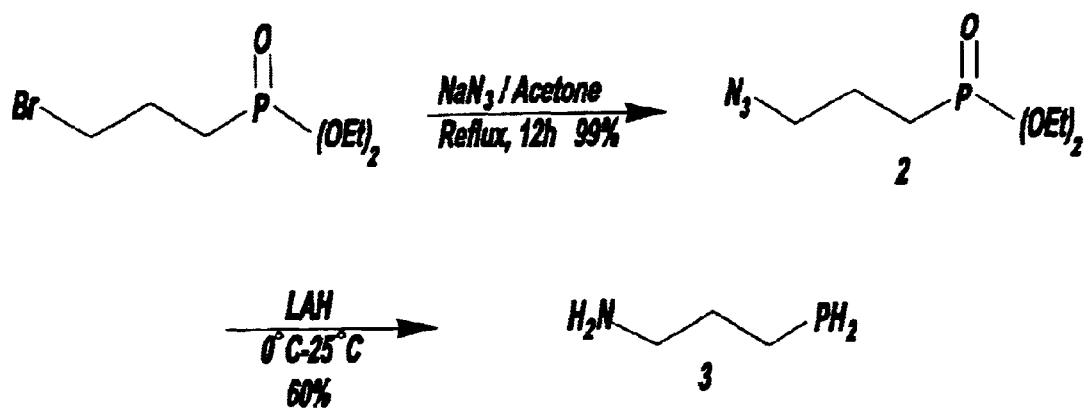
FIG. 3 is a detailed depiction of Scheme 1.
Figure 4:
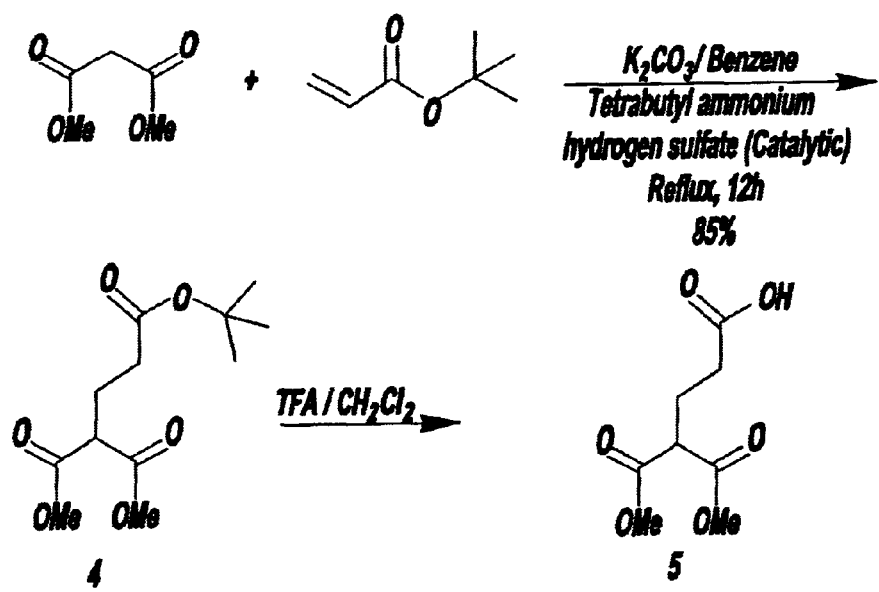
FIG. 4 is a detailed depiction of Scheme 2.
Figure 5:
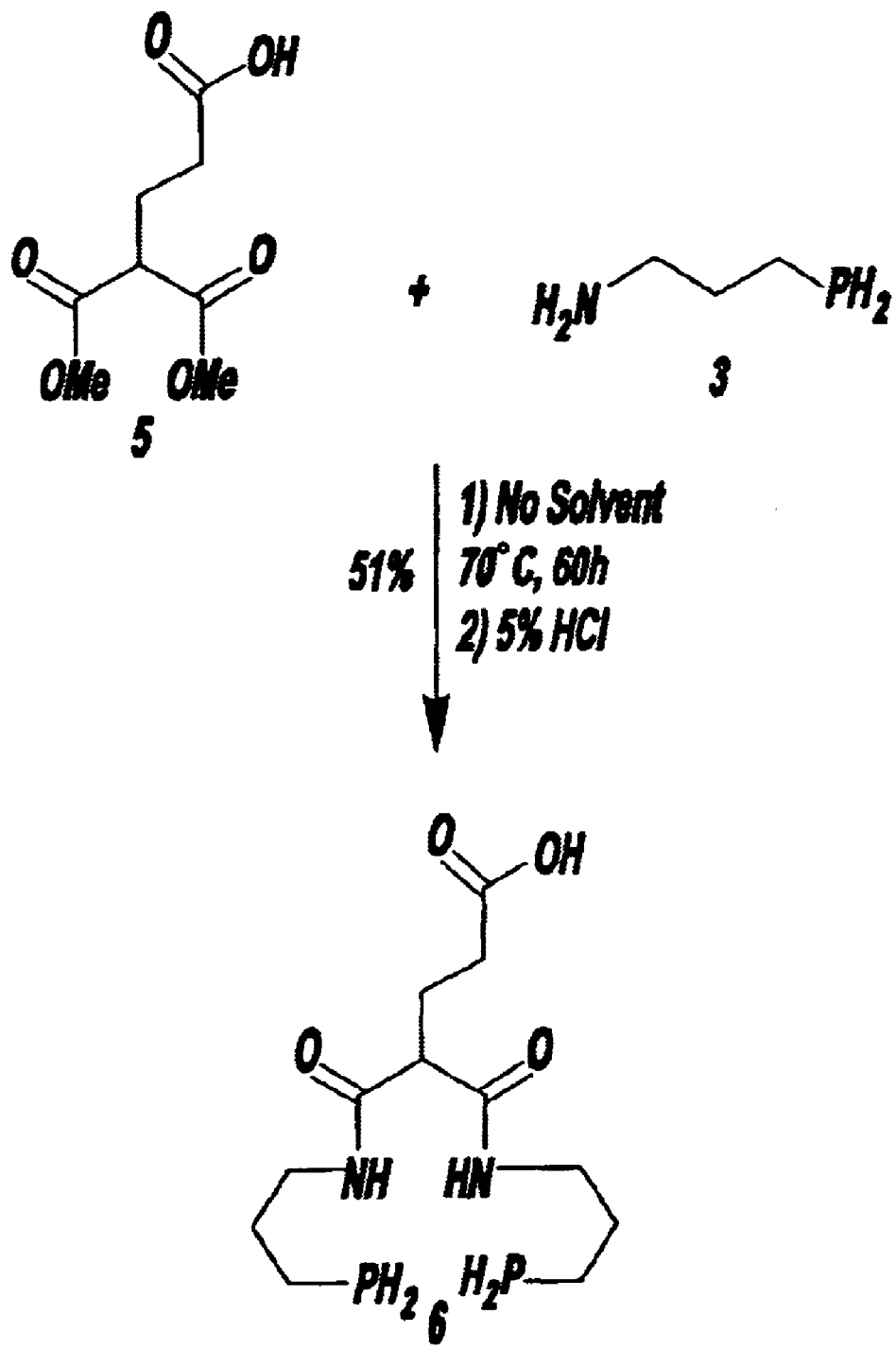
FIG. 5 is a detailed depiction of Scheme 3.

The use of —$PH_2$ synthons to form —$P(CH_2OH)_2$ based ligands was explored. Initial studies with $NH_2$—$(CH_2)_3PH_2$ reactant (synthesized in the laboratory) demonstrated that it was possible to produce the $P_2N_2$—BFCA (shown in FIG. 1) without going through the reduction step late in the synthetic scheme (see Schemes 1, 2, and 3; FIGS. 3, 4 and 5) [7]. Utilization of the $NH_2$—$(CH_2)_3PH_2$ intermediate in this fashion was rather facile. This was unexpected, since phosphorus hydrides (e.g., —$PH_2$ containing compounds) are known to have poor oxidative stability. However, these initial synthesis were carried out in organic solvents and care was taken to remove molecular oxygen, except for the rapid conversion of the —$PH_2$ groups to the —$P(CH_2OH)_2$ groups by the addition of water containing traces of $H_2CO$ [7].

The potential of using HMP-based chelating frameworks for labeling biomolecules with radioactive transition metals (including $^{99m}Tc$ and $^{188}Re$) has been explored. Recent studies demonstrate that $^{99m}Tc$- and $^{188}Re$-complexes with the $P_2N_2$—COOH BFCA (FIG. 2) are stable under in vivo conditions (Table 1 and 2) [7]. These data provide important evidence that HMP-based metal chelates are useful systems for conjugating biomolecules with transition metals for a variety of chemical and biological applications. Work with $^{99m}Tc$- and $^{188}ReP_2N_2$-bioconjugates and other model HMP-based chemical system has demonstrated that HMP-containing ligand frameworks hold an important place in the formulation of new diagnostic and therapeutic radiopharmaceuticals [7].

Conjugations of the functionalized hydroxymethyl phosphines or their radiometal complexes to specific biomolecules requires incorporation of a reactive functionality (e.g. —COOH) on their backbone. The synthetic methodology used to produce the functionalized hydroxymethyl phosphines precludes the incorporation of —COOH because it involves a reduction step that uses $LiAlH_4$ and $LiAlH_4$ would also reduce the —COOH to —$CH_2OH$ [Smith et al., 1997].

This inherent synthetic difficulty necessitated the development of a novel synthetic strategy wherein a preformed phosphorus(III) hydride, $BrCH_2CH_2CH_2PH_2$, interacts (and alkylates) within a carboxylate functionalized organic anion (dihydrolipoic acid). The synthesis and characterization of the inventive bifunctional chelating agent derived from phosphine building units, as taught herein, is shown below in Scheme 1 and Scheme 2.

As a result of working with the $NH_2(CH_2)_3$ $PH_2$ intermediate, it was recognized that the intermediate was unexpectedly stable under a variety of storage and reaction conditions. $NH_2(CH_2)_3$ $PH_2$ was reasonably stable in a variety of solvents and over a wide pH range and temperature range. For example, $PH_3$ and the simple methyl- and ethyl-$PH_2$ molecules exhibit poor oxidative stability.

When this analogue was studied under an even wider range of chemical conditions than that used with the $NH_2$ $(CH_2)_3$ $PH_2$ intermediate, (see Experimental), the analogue exhibited a much improved stability profile. Furthermore, the reactivity of the —$PH_2$ groups in these compounds toward molecules containing a wide spectrum of functional groups (including carboxylic acids, amines, thiols, and proteins) was remarkably low or non-measurable. To the Applicants' knowledge, this constitutes the first disclosure of compounds containing —$PH_2$ groups that exhibit the degree of stability and non-reactivity which is set forth in this application.

Results of these studies suggested the possibility that appropriate —$PH_2$ containing compounds are useful for synthesis of —$PH_2$ containing biomolecules, either via linking —$PH_2$ groups to or incorporation of —$PH_2$ groups in the biomolecular structure.

Figure 2:
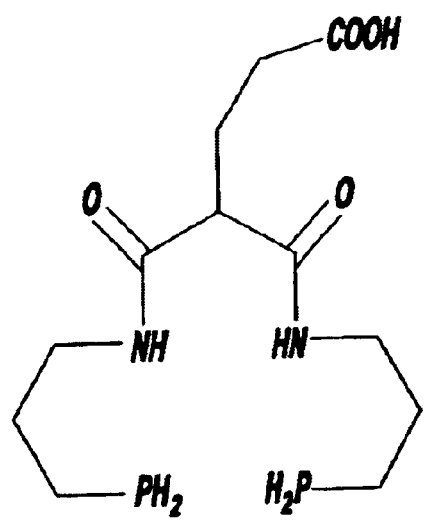
FIG. 2 is the chemical formulation of a diiphosphorus hydride-diamide-COOH BFCA ($P_2N_2$—COOH BFCA), a —$PH_2$ analogue of the $P_2N_2$—BFCA shown in FIG. 1.

In order to determine the feasibility of linking —$PH_2$ group-containing compounds to biomolecules, the —COOH group on the $(PH_2)_2$—$N_2$—COOH bifunctional chelating agent shown in FIG. 2 above was activated (i.e., HBTU activator) and subsequently reacted with the free primary amine group on peptides to form an amine linkage. In one case, the activated bifunctional chelating agent reacted with the N-terminal amine group on diglycine. After synthesis and purification, the —PH$_2$ diglycine conjugate was shown to be formed in high yields with the —PH$_2$ groups remaining intact.

These results demonstrate that the —PH$_2$ groups on this bifunctional chelating agent are resistant to oxidation and have no reactivity with any functional groups on the LH-RH peptide or with the chemicals used during SPPS and analysis. These data also provide evidence that —PH$_2$ groups appended to likely chemical backbones can be used as synthetic intermediates to synthesize —PH$_2$ group-conjugated biomolecules.

The reasons for the unexpectedly high oxidative stability of —PH$_2$ groups and low chemical reactivity are not fully understood. However, appending the —PH$_2$ groups, via a hydrocarbon backbone, to larger molecular backbones can produce major deactivation of the oxidative and chemical reactivity of these groups.

After synthesis of —PH$_2$ derivatized biomolecules, it is possible to convert the —PH$_2$ groups to other phosphines including, for example, HMP groups. Aldehyde groups are one class of functionalities that will react rapidly with —PH$_2$ groups. Thus, the —PH$_2$ groups can be converted, in a rapid and facile manner (e.g., in aqueous solutions over a wide -pH range), by reaction with aldehydes to produce the corresponding —PR$_2$ groups.

For example, formaldehyde rapidly reacts with —PH$_2$ groups to form —P(CH$_2$OH)$_2$ groups. Either the —PH$_2$ groups or the —PR$_2$ groups (converted from —PH$_2$ groups) can be used as part of a chelator framework on the biomolecule, to form well defined, stable complexes with transition metals to produce the metallated conjugate.

It is possible to synthesize biomolecules, for example, steroids, peptides and proteins, with chiral centers at specific points in their backbone. Incorporation of ligating centers capable of coordination with catalytically useful transition metals, for example, Rh(I), Pd(II), and Re(I–V) at specific positions of chiral biomolecules lead to the design and development of enautioselective transition metal catalysts. Incorporation of alkyl or aryl phosphine ligands on biomolecules was previously difficult because under the reaction conditions that were employed, for example, dimethyl formamide solvent, or trifluoroacetic treatment, phosphines are oxidized to their corresponding phosphine oxides. In this context, the utility of phosphines, in the form of PH$_2$ precursors, as described in Schemes 1 and 2 (FIGS. 3 and 4) above is unique.

This present invention also provides avenues for the incorporation of chiral centers on phosphine backbones. The resulting transition metal complexes of chiral center functionalized phosphines are important due to applications as enautioselective catalysts in the synthesis of fine chemicals and pharmaceutical intermediates.

Thus, according to the present invention, —PH$_2$ containing reagents (synthons) provide an important new approach for syntheses of —PH$_2$ containing biomolecules by virtue of their unexpectedly high oxidative stability and low chemical reactivity. The —PH$_2$ groups can be readily converted to other —PR$_2$ functionalities, for example, R=—CH$_2$OH. Without the use of this new synthetic approach it is extremely difficult, if not impossible, to synthesize —PR$_2$ containing biomolecules. These phosphine groups appended to biomolecules at selected molecular sites can be used to complex transition metal conjugates. Examples of $^{99m}$Tc complexation reactions with biomolecule conjugated (P$_2$H$_2$)$_2$S$_2$ ligands are outlined in Scheme 6. These metallated biomolecules can be used in a variety of chemical applications, including but not limited to, for example, chiral catalysts, and biomedical applications, including but not limited to, for example, radiopharmaceutical applications [Gilbertson et al., 1996; Liu et al., 1997; Lister-James, et al., 1997; Gilbertson, et al., 1994].

EXAMPLES

Experimental Section

Materials. All chemicals were obtained from either Aldrich Chemical Co. or Fisher Scientific. The chemicals and solvents were of reagent grade and used without further purification. A $^{188}$W/$^{188}$Re generator was obtained from Missouri University Research Reactor and eluted using normal saline. CF-1 normal mice were purchased from Taconic Labs. ReO$_2$(py)$_4$Cl was synthesized as reported in the literature. Nuclear magnetic resonance spectra were recorded on a Bruker ARX-300 spectrometer. The $^1$H and $^{13}$C chemical shifts are reported relative to residual solvent protons are a reference, while the $^{31}$P shifts are reported relative to an external reference of 85% H$_3$PO$_4$. IR spectra were recorded on a Mattson Galaxy Series FTIR 3000 spectrometer. FAB-Mass spectral analyses were performed by the mass-spectrometry laboratories at Washington University, St. Louis, Mo.

HPLC Analysis. HPLC analyses were performed on a Waters 600E system equipped with a Waters 486 tunable absorption detector, a radiometric detector system, and a Waters 746 Data Module integrating recorder. HPLC solvents consisted of water containing 0.1% trifluoroacetic acid (solvent A) and acetonitrile containing 0.1% trifluoroacetic acid (solvent B). For the radiochemical experiments (analysis and purification) a C-18 Hamilton PRP-1 column (10 μm, 150×4.1 mm) was used. The HPLC gradient system started with 95% A/5% B from zero to two minutes followed by a linear gradient 95% A/5% B to 100% B from two to seven minutes. The gradient remained at 100% B for two minutes before ramping back to 95% A/5% B in seven minutes. The flow rate was 1.5 ml/minute.

Experimental Section

A. Synthetic Procedures

Preparation of Diethyl-3-azidopropyl Phosphonate 2 (Scheme 1, FIG. 3):

To a well-stirred solution of diethyl-3-bromopropyl phosphonate (30 g, 115 m mol) in acetone (100 ml), sodium azide (15 g, 230 mmol) was added at room temperature (23° C.) under a nitrogen atmosphere. The reaction mixture was refluxed for twelve hours, cooled to room temperature, filtered and then solvent was removed under vacuum to afford diethyl-3-azidopropyl phosphonate, 2 as a colorless liquid. The purity was determined by NMR ($^1$H, $^{13}$C, and $^{31}$P). The crude was sufficiently pure to carry over to the next step. The yield is 25.5 g (99%) which is analyzed as follows: $^1$H (CDCl$_3$, 300 mHz): δ 4.2–4 (m, 4H), 3.4 (2H, t, J=6.2 Hz), 1.95–1.7 (m, 4H), 1.3 (6H, t, J=6.9 Hz) $^{13}$C (CDCl$_3$, 75 MHz): δ 61.3, 50.9 (d, J=16 Hz), 22.32 (d, J=143 Hz), 21.9, 16.0 $^{31}$P (CDCl$_3$, 121 MHz)): δ 32.2; with a mass (m/z): 222.2 (M+1)$^+$, HRMS, Calcd. 222.1007 Found 222.1005.

Preparation of 3-Aminopropylphosphine 3 (Scheme 1, FIG. 3):

To a vigorously stirred cold (0° C.) solution of lithium aluminum hydride (230 ml, 1M solution in ether) there was added a solution of diethyl-3-azidopropyl phosphonate 2 (30 g, 135 ml)) in ether (60 ml) over one hour under nitrogen atmosphere. The stirring mixture was allowed to warm to room temperature and was stirred at room temperature for five hours. The reaction mixture was cooled to 0° C. and the excess of lithium aluminum hydride was quenched by slow addition of cold aqueous brine solution (10 ML), followed by the addition of aqueous KOH solution (10%, 20 ML). The reaction mixture was brought to room temperature with vigorous stirring. The organic layer was separated, the reaction mixture was extracted with ether (3×300 ML), the combined organic extract was washed with brine (100 ML), dried over anhydrous sodium sulfate, and the solvent was removed by fractional distillation under atmospheric pressure to afford 3-Aminpropylphosphine, 3 as a colorless liquid. The yield is 7.4 g* (60%), with a BP as follows: $^1$H (CDCl$_3$, 300 MHz): δ 5.2 (bs, 2H), 2.8 (t, 2H, J=6.7 Hz), 2.76 (dt. J=194 Hz, J=7.4 Hz), 1.8–1.6 (m, 2H), 1.6–1.5 (m, 2H); $^{13}$C (CDCl$_3$, 75 MHz): δ 41.7, 35.8, and 10.3; $^{31}$P (CDCl$_3$, 121 MHz)): δ −135.7.

Preparation of Dimethyl-2-(3-t-butyl Propionyl) Malonate 4 (Scheme 2, FIG. 4):

The mixture of Diethyl malonate (25 g, 189 mmol), t-butyl acrylate (24.23 g, 189 mmol), potassium carbonate (26.12 g, 189 mmol) and tetrabutylammonium hydrogen sulfate (700 mg, 1.9 mmol) in benzene (100 ml) were heated at reflux for 16 hours. This was cooled to room temperature, filtered and the solvent was evaporated to furnish the crude product 4. The crude product was distilled under reduced pressure to afford the pure product 4 as a colorless oil. The yield was 40 g (85%), which had the following characteristics: BP: 120° C./0.1 mm; $^1$H (CDCl$_3$, 300 MHz): δ 3.74 (s, 6H), 3.48 (t, 1H, J=6.4 Hz), 2.31(t, 2H, J=7.2 Hz), 2.16 (m, 2H), 1.45 (s, 9H); $^{13}$C (CDCl$_3$, 75 MHz): δ 171.4, 169.2, 80.4, 52.3, 50.2, 32.4, 27.8, and 23.8; and a mass (m/z): 261.4 (M+1)$^+$, HRMS, Calcd. 261.1338 Found 261.1331.

Preparation of Dimethyl-2-(3-propionic Acid) Malonate 5 (Scheme 2, FIG. 4):

Dimethyl-2-(3-t-butyl propionyl) malonate 4 (5 g, 19.2 mmol) and trifluro acetic acid (100 ml) in dichloromethane (100 ml) was stirred at room temperature for ten hours, trifluro acetic acid and dichloromethane were removed under vacuum to form the corresponding acid 5 as a colorless oil. The yield was 3.8 g (97%). The analysis also discovered the following characteristics: $^1$H (CDCl$_3$, 75 MHz): δ 3.76 (s, 6H), 3.54 (t, 2H, J=7.3 Hz), 2.5 (t, 2H, J=7.4 Hz), 2.28–2.1 (m, 2H); $^{13}$C (CDCl$_3$, 75 MHz): δ 178.8, 169.5, 52.8, 50.3, 31.1, and 23.4; with a mass (m/z): 205.2 (M+1)$^+$, HRMS, Calcd. 205.0712 Found 205.0710.

Preparation of N$_2$P$_2$COOH 6 (Scheme 3, FIG. 5):

Dimethyl-2-(3-propionic acid) malonate 5 (2 g, 9.8 mmol) and 3-Aminopropylphosphine 3 (2.85 g, 31.4 mmol) were heated at 70° C. for 60 hours under nitrogen atmosphere and the excess of 3-Aminopropylphosphine was removed under vacuum. The reaction mixture was dissolved in water (5 ml), cooled to 0° C. and neutralized by 2N Hydrochloric acid (5 ml) to form a white solid which was filtered, washed with water, dried and purified by flash column chromatography (silica gel, CH$_3$OH: CHC13, 1:20) under nitrogen to afford the corresponding N2P2COOH 6 as white solid. The yield was 1.6 g (51%), and had the following characteristics: $^1$H (CDCl$_3$, 300 MHz): δ 7.5 (bs, 2H), 3.48 (t, 1H, J=7.7 Hz), 3.3–3.2 (m, 4H), 3.0 (dt, 4H, J=194 Hz, J=7.4 Hz), 2.38 (m, 2H), 2.2–2.1 (m, 2H), 1.8–1.63 (m, 4H), 1.6–1.4 (m, 4H); $^{13}$C (CDCl$_3$75 MHz): δ 175.6, 171.2, 52.1, 40.2, 32.5, 31.6, 27.3, and 11.2; $^{31}$P (CDCl$_3$, 121 MHz): δ −135.6; mass (m/z): 323.4 (M+1)$^+$, HRMS, Calcd. 323.1289 Found 323.1288.

Conjugation of N$_2$P$_2$COOH 6 with GlyGlyethyl Ester Hydrochloride (Scheme 4, FIG. 6):

To a well-stirred solution of N2P2 COOH 6 (100 mg, 0.31 mmol) in CH$_3$CN (15 ML) under nitrogen atmosphere was added GlyGlyethylester hydrochloride (61 mg, 0.31 mmol) followed by triethylamine (63 mg, 0.62 mmol). After ten minutes HBTU (120 mg, 0.31 mmol) was added and the reaction mixture was stirred for twelve hours. The solvent was removed under reduced pressure to afford the crude product which was purified by a flash column (silica gel, 8% methanol chloroform) to furnish the corresponding conjugate as a white solid. This yielded 86 mg (60%), which were characterized as follows: $^1$H (CDCl$_3$, 300 MHz): δ 8.0 (bt, 1H), 7.5 (bt, 1H). 7.0 (bt, 1H), 4.2 (2H, q, J=7.2 Hz), 4.18 (d, 2H, J=5.6 Hz), 4.0 (d, 2H, J=6.2 Hz), 3.4 (t, 1H, J=8.2 Hz), 3.3–3.15 (m, 4H), 2.71 (dt, 4H, J=194, 7.3 Hz), 2.35–2.3 (m, 2H), 2.25–2.15 (m, 2H), 1.8–1.6 (m, 4H), 1.55–1.4 (m, 4H), 1.3 (t, 3H, J=7.1 Hz); $^{13}$C (CDCl$_3$, 75 MHz): δ 172.8, 171.4, 171.0, 61.7, 51.4, 43.4, 41.0, 40.0, 33.7, 32.7, 29.6, 14.2, 11.2; and a mass (m/z): 465, HRMS Calcd. 465.1953 Found 465.2041.

Preparation of N$_2$P$_2$COOH HMP (Scheme 5, FIG. 7)

To a solution of N$_2$P$_2$COOH (500 mg, 1.55 mmol) in degassed ethanol (2 ml), 37% aqueous formaldehyde solution (503 mg, 6.2 mmol) was added dropwise and stirred to room temperature (25° C.) for fifteen minutes under nitrogen. Removal of the solvent under reduced pressure afforded N$_2$P$_2$COOH HMP (670 mg, 98%) as a colorless viscous oil. The $^{31}$P NMR (121 MHz, D$_2$O) showed a δ=−22.71 (s). For characterization and all other studies purpose, N$_2$P$_2$COOH HMP was converted into bisphosphonium chloride salt by the addition of 5N hydrochloric acid (0.5 ml) and 37% aqueous formaldehyde (252 mg, 3.1 mmol) to a solution of bis(hydroxymethyl) phosphine (670 mg, 1.53 mmol) in degassed ethanol (5 ml) at room temperature (25° C.). After the removal of solvent under reduced pressure, the crude product was chromatographed on a C-18 Sep-Pak reverse phase column with water/methanol solvent system to obtain a pure bisphosphonium chloride (827 mg, 95%) as a colorless viscous oil. The $^{31}$P NMR (121 MHz, D$_2$O) showed a δ=30.72 (s).

Figure 8:
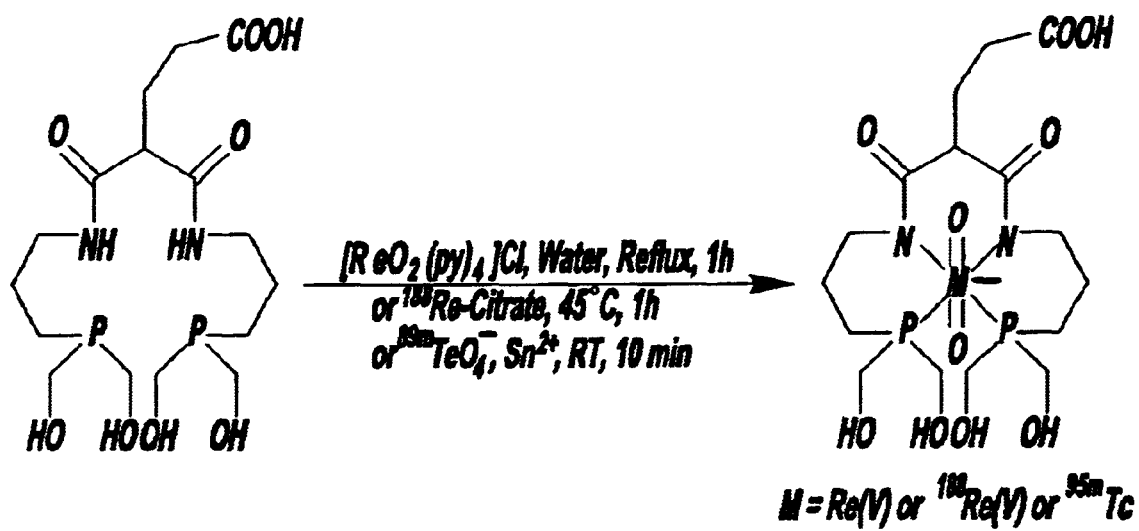
FIG. 8 is a detailed depiction of Scheme 6.

Preparation of ReO$_2$—N$_2$P$_2$COOH Complex (Scheme 6, FIG. 8)

A solution of P$_2$N$_2$COOH HMP (650 mg, 1.47 mmol) in water (50 ml) was added to a solution of [ReO$_2$(py)$_4$]Cl (py=pyridine) (790 mg, 1.46 mmol) in water (100 ml) and the reaction mixture was refluxed for one hour. The reaction solution was concentrated and purified on a reverse phase Sep-Pak C-18 column (35 cc, 10 g) using a water-methanol gradient to obtain a pure [ReO$_2$—N$_2$P$_2$COOH][C5H$_6$N] complex which has a brown colored solid. The yield was 985 mg (83%). The analytical data showed a LR-FAB mass m/z of 740.2 [M+1]$^+$; 661.1 [M-C$_5$H$_6$N+2]$^+$; 659.1[M-C$_5$H$_6$N]$^-$, HR-FAB mass m/z [M—C$_5$H$_6$N]$^-$; calc. 659.0934 found 659.0942; IR (NaCl), cm$^{-1}$; 910 (s, v$_s$O═Re═O); 797 (s, v$_{as}$ O═Re═O); $^1$H NMR (300 MHz, D$_2$O): δ=8.67–8.60 (m, 2H), 7.82 (t, J=7.6 Hz, 1H), 7.40–7.36 (m, 2H), 4.68–4.45 (m, 1H), 4.29–3.91 (m, 8H), 3.68–3.48 (m, 2H), 3.24–2.95 (m, 4H), 2.25–2.14 (m, 4H), 2.14–2.02 (bs, 4H), 2.02–1.89 (m, 4H), 1.75 (bs, 4H); $^{13}$C NMR (75 MHz, D$_2$O): δ=172.5 (s), 149.4 (s), 142.8 (s), 127.5 (s), 58.5 (t), 58.9 (s), 54.5 (s), 40.6 (s), 33.1 (s), 25.5 (s), 24.4 (s), 21.2 (s), 20.8 (s); $^{31}$P NMR (121 MHz, D$_2$O): δ=−4.4 (s).

B. Radiolabelling Procedures $^{188}$Relabeling of N$_2$P$_2$COOH BFCA

Preparation of the ligand stock solution includes 5 mg (11.3 μmol) of P$_2$N$_2$COOH HMP which was dissolved in 1 ml of $H_2O$. 200 μl of the 1M sodium citrate solution was added to 500 μl of $Na[^{188}ReO_4]$ in saline. This mixture was then vortexed. The rhenium was reduced by the addition of 15 mg stannous chloride and the solution was heated at 90° C. for 30 minutes to form $^{188}Re$-citrate. Then 50 μl of ligand stock solution was added and heated at 45° C. for 30 minutes to form the $^{188}Re$-$P_2S_2COOH$ complex. The formation of the product was confirmed by HPLC (>95% yield). The retention times of $Na[^{188}ReO_4]$ and 188Re-citrate are 1.5 minutes and 1.0 minutes respectively, whereas the $^{188}Re$—$P_2N_2COOH$ complex had a retention time of 7.2 minutes.

In vitro Studies of $^{188}Re$—$N_2P_2COOH$ Complex

The stability of the complex at pH=5, 7 and 9 was determined at various time points (2 hours, 5 hours and 20 hours) post complexation. Radiochemical purity (%RCP) was determined by using HPLC. The samples are injected on the HPLC with the above mentioned gradient system. The elution of >95% of the injected activity excluded the presence of measurable $^{188}ReO_2$ or the $^{188}Re$-compounds which cannot be eluded from the column. It was found that the $^{188}Re$—$P_2N_2COOH$ complex is stable in pH ranging 5–9 over 20 hours with >95%RCP.

In vivo Studies of $^{188}Re$—$N_2P_2COOH$ Complex in Normal Mice

Normal CF-1 mice (average weight, 25 g) were used for the biodistribution studies (Table 1 and 2). The pH of the HPLC-purified $^{188}Re$—$P_2N_2COOH$ solution was adjusted to physiological conditions using a 0.01M phosphate buffer (pH=7.4). 80–100 μl aliquots of $^{188}Re$—$P_2N_2COOH$ solution (55–75 kBq) was injected in each animal via the tail vein. Tissues and organs were excised from the sacrificed animals at one hour and two hours p.i. The organs and tissue were weighed and the activity counted in NaI counter. The percent injected dose per organ and the percent injected dose per gram were calculated. The % ID in whole blood was estimated assuming a blood volume of 6.5% of the total body weight.

Throughout this application, various publications, are referenced by author and year. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of labeling a biomolecule with a transition metal or radiometal in a site-specific manner to produce a diagnostic or therapeutic pharmaceutical compound comprising the steps of:

synthesizing a $P_2N_2$-bifunctional chelating agent intermediate;

complexing the intermediate with a radiometal or a transition metal; and covalently linking the resulting metal-complexed bifunctional chelating agent with a biomolecule.

2. A method of synthesizing —$PR_2$ containing biomolecules comprising the steps of:

synthesizing a $P_2N_2$— bifunctional chelating agent intermediate;

complexing the intermediate with a radiometal or a transition metal; and covalently linking the resulting metal-complexed bifunctional chelating agent with a biomolecule, wherein R is selected from the group consisting of H and $CH_2OH$.

3. A therapeutic or diagnostic comprising a —$PR_2$ containing biomolecule, wherein R is selected from the group consisting of H and $CH_2OH$.

4. The therapeutic or diagnostic according to claim 3, wherein said biomolecule is selected from the group consisting essentially of a steroid, a peptide, and a protein.

5. The therapeutic or diagnostic according to claim 3, wherein said biomolecule further includes a metal selected from the group consisting essentially of radiometals and transition metals.

* * * * *